(12) United States Patent  
Geiger

(10) Patent No.: US 7,081,088 B2
(45) Date of Patent: Jul. 25, 2006

(54) METHOD AND APPARATUS FOR AUTOMATIC LOCAL PATH PLANNING FOR VIRTUAL COLONOSCOPY

(75) Inventor: Bernhard Geiger, Cranbury, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 449 days.

(21) Appl. No.: 10/753,703

(22) Filed: Jan. 8, 2004

(65) Prior Publication Data

US 2004/0209234 A1   Oct. 21, 2004

Related U.S. Application Data

(60) Provisional application No. 60/470,579, filed on May 14, 2003, provisional application No. 60/443,734, filed on Jan. 30, 2003.

(51) Int. Cl.
*A61B 1/00* (2006.01)
*A61B 5/05* (2006.01)
*G06T 15/10* (2006.01)

(52) U.S. Cl. .................. 600/103; 600/416; 345/427
(58) Field of Classification Search ............... 600/101, 600/103, 117, 118, 416, 419, 427
See application file for complete search history.

(56) References Cited

U.S. PATENT DOCUMENTS

| 5,611,025 | A   | * | 3/1997  | Lorensen et al. | 345/419 |
| 6,690,816 | B1  | * | 2/2004  | Aylward et al.  | 382/128 |
| 6,928,314 | B1  | * | 8/2005  | Johnson et al.  | 600/407 |
| 2001/0031920 | A1 | * | 10/2001 | Kaufman et al. | 600/431 |
| 2005/0033114 | A1 | * | 2/2005  | Geiger et al.  | 600/101 |
| 2005/0107679 | A1 | * | 5/2005  | Geiger et al.  | 600/407 |

OTHER PUBLICATIONS

Paik, David S., et al, Automated flight planning for virtual endoscopy, Med. Phys. 25 (5), May 1998, pp. 629-637.*

* cited by examiner

*Primary Examiner*—John Leubecker
*Assistant Examiner*—Philip R. Smith
(74) *Attorney, Agent, or Firm*—Donald B. Paschburg

(57) ABSTRACT

A method for automatic local path planning for a virtual endoscope comprises the steps of defining a sub volume around a current endoscope position in a lumen; performing a region growing inside the lumen, starting from the current endoscope position; calculating and clustering the intersection of the region with the faces of a cube circumscribing the sub volume; calculating approximated centerline paths from the current endoscope position to the center of each cluster formed in the preceding step; comparing each of the centerline paths with a current path exhibited by the endoscope; and selecting an optimal centerline path based on the comparison.

34 Claims, 2 Drawing Sheets

METHOD AND APPARATUS FOR AUTOMATIC LOCAL PATH PLANNING FOR VIRTUAL COLONOSCOPY

CROSS-REFERENCE TO RELATED APPLICATIONS PRIORITY

Specific reference is hereby made to copending U.S. Provisional Patent Application No. 60/443,734, filed in the United States Patent and Trademark Office on Jan. 30, 2003 in the name of inventor Bernhard Geiger, and entitled AUTOMATIC LOCAL PATH PLANNING FOR VIRTUAL COLONOSCOPY, whereof the disclosure is hereby incorporated by reference herein, and whereof the benefit of priority is claimed.

Specific reference is also hereby made to copending U.S. Provisional Patent Application No. 60/470,579, filed in the United States Patent and Trademark Office on May 14, 2003 in the name of inventors Bernhard Geiger and Jean-Daniel Boissonnat, and entitled FAST CENTERLINE EXTRACTION, whereof the disclosure is hereby incorporated by reference herein, and whereof the benefit of priority is claimed.

The present application relates generally to computer vision and imaging systems and, more particularly, to a system and method for automatic local path planning such as may be utilized for virtual endoscopy and virtual colonoscopy.

BACKGROUND OF THE INVENTION

Virtual colonoscopy (VC) refers to a method of diagnosis based on computer simulation of standard, minimally invasive endoscopic procedures using patient specific three-dimensional (3D) anatomic data sets. Examples of current endoscopic procedures include bronchoscopy, sinusoscopy, upper gastro-intestinal endoscopy, colonoscopy, cystoscopy, cardioscopy, and urethroscopy. VC visualization of non-invasively obtained patient specific anatomic structures avoids risks, such as perforation, infection, hemorrhage, and so forth, associated with real endoscopy, and provides the endoscopist with important information prior to performing an actual endoscopic examination. Such understanding can minimize procedural difficulties, decrease patient morbidity, enhance training and foster a better understanding of therapeutic results.

In virtual colonoscopy, 3D images are created from two-dimensional (2D) computerized tomography (CT) or magnetic resonance (MR) data, for example, by volume rendering.

These 3D images are created to simulate images coming from an actual endoscope, such as a fiber optic endoscope. This means that a viewpoint of the virtual endoscope has to be chosen inside a lumen of the organ or other human structure, and with a wide angle of view, typically about 100 degrees of arc. This viewpoint has to move along the inside of the lumen, which means that a 3D translation and a 3D rotation have to be applied. Controlling these parameters interactively is a challenge.

A commonly used technique for navigating a viewpoint of a virtual endoscope is to calculate a "flight path" beforehand and automatically move the viewpoint of the virtual colonoscope along this path. However, this technique requires a segmentation and trajectory calculation step that is time-consuming and can fail.

Applicant's prior patent application Ser. No. 10/322,326, filed Dec. 18, 2002, and entitled AUTOMATIC NAVIGATION FOR VIRTUAL ENDOSCOPY and whereof the disclosure is hereby incorporated herein by reference to the extent it is not incompatible with the present invention, discloses a system and method of navigation inside a colon dataset, using the longest view ray to advance. The aforesaid prior patent application shows a system and method for automatic navigation of a viewpoint of an endoscope in virtual colonoscopy is provided. The system determines automatically a direction and orientation of a virtual endoscope. Therefore a user needs to control only one parameter—forward or backward speed and the method allows immediate interactive navigation inside an organ without preprocessing, e.g. segmentation and path generation. The method shown in the said application includes the steps of (a) determining an initial viewpoint of the virtual endoscope, the initial viewpoint having a first center point and a first direction; (b) determining a longest ray from the initial viewpoint to the lumen, the longest ray having a first longest ray direction; (c) determining a second direction between the first direction of the initial viewpoint and the first longest ray direction; (d) turning the viewpoint to the second direction and moving the initial viewpoint a first predetermined distance in a first direction of the initial viewpoint; (e) calculating a second center point of the viewpoint; (f) moving the viewpoint to the second center point; and repeating steps (b) through (f) until the viewpoint reaches an intended target.

BRIEF SUMMARY OF THE INVENTION

It is herein recognized that it is nevertheless possible, under certain circumstances, for operation of the system disclosed in the aforesaid prior patent application Ser. No. 60/343,012, to get stuck in a sharp bend, or a deep Haustral fold as may occur in virtual colonoscopy.

According to one aspect of the present invention, a method for navigating a viewpoint of a virtual colonoscope in a lumen of a structure is provided. In accordance with an aspect of the present invention, a method for automatic path planning comprises the following steps: defining a sub volume around the current endoscope position; performing a region growing inside the lumen, starting from the endoscope position; calculating and clustering the intersection of the grown region with the 6 faces of a cube circumscribing the region of interest; calculating approximated centerlines from the endoscope position to the center of each of the clusters; comparing each path with the current path of the endoscope; and finding the best score.

In accordance with another aspect of the invention, a method for automatic local path planning for a virtual endoscope, comprises the steps of: deriving a colon dataset obtained by a colonoscopy protocol for utilization in subsequent steps; defining a sub volume around a current endoscope position in a lumen; performing a region growing inside the lumen, starting from the current endoscope position; calculating and clustering the intersection of the region with the faces of a cube circumscribing the sub volume; calculating approximated centerline paths from the current endoscope position to the center of each cluster formed in the preceding step; comparing each of the centerline paths with a current path exhibited by the endoscope; assigning a score based on the comparing, to each of the centerline paths; and selecting a centerline path based on the score.

In accordance with another aspect of the invention, the step of deriving a colon dataset obtained by a colonoscopy protocol comprises deriving the data set by computerized tomography (CT).

In accordance with another aspect of the invention, the step of deriving a colon dataset obtained by a colonoscopy protocol comprises deriving the data set by magnetic resonance (MR).

In accordance with another aspect of the invention, a method for automatic local path planning for a virtual endoscope includes a step of defining the cube to be of a given number of voxels centered around the current endoscope.

In accordance with another aspect of the invention, a step of calculating approximated centerline paths comprises: calculating an initial path; and centering and smoothing the initial path.

In accordance with another aspect of the invention, a step of centering and smoothing the initial path comprises using Gaussian smoothing.

In accordance with another aspect of the invention, a step of centering and smoothing the initial path comprises: setting a sphere at a vertex location; increasing the size of the sphere size until it comes into collision with a wall of the lumen; calculating a translation force from the collision; applying the translation force until the sphere is no longer in collision; increasing the size of the sphere and it again comes into further collision with the wall; calculating a further translation force; applying the further translation force until the sphere is no longer in collision; repeating the foregoing three steps until the sphere reaches a final position where it cannot grow any more without collision; indicating the final position as a final vertex position.

In accordance with another aspect of the invention, a method for automatic local path planning for a virtual endoscope, comprises the steps of: deriving a colon dataset obtained by a colonoscopy protocol for utilization in subsequent steps; defining a sub volume around a current endoscope position in a lumen; performing a region growing inside the lumen, starting from the current endoscope position; calculating and clustering the intersection of the region with the faces of a cube circumscribing the sub volume; calculating approximated centerline paths from the current endoscope position to the center of each cluster formed in the preceding step by: calculating an initial path; centering and smoothing the initial path; comparing each of the centerline paths with a current path exhibited by the endoscope; assigning a score based on the comparing, to each of the centerline paths; and selecting a centerline path based on the score.

In accordance with another aspect of the invention, a method for automatic local path planning for a virtual endoscope, comprising the steps of: defining a sub volume around a current endoscope position in a lumen; performing a region growing inside the lumen, starting from the current endoscope position; calculating and clustering the intersection of the region with the faces of a cube circumscribing the sub volume; calculating approximated centerline paths from the current endoscope position to the center of each cluster formed in the preceding step; comparing each of the centerline paths with a current path exhibited by the endoscope; and selecting an optimal centerline path based on the comparing.

In accordance with another aspect of the invention, a system for automatic local path planning for a virtual endoscope, comprises: apparatus for defining a sub volume around a current endoscope position in a lumen; apparatus for performing a region growing inside the lumen, starting from the current endoscope position; apparatus for calculating and clustering the intersection of the region with the faces of a cube circumscribing the sub volume; apparatus for calculating approximated centerline paths from the current endoscope position to the center of each cluster formed in the preceding step; apparatus for comparing each of the centerline paths with a current path exhibited by the endoscope; and apparatus for selecting an optimal centerline path based on the comparing.

In accordance with another aspect of the invention, a system for automatic local path planning for a virtual endoscope, comprises: apparatus for deriving a colon dataset obtained by a colonoscopy protocol for utilization in subsequent steps; apparatus for defining a sub volume around a current endoscope position in a lumen; apparatus for performing a region growing inside the lumen, starting from the current endoscope position; apparatus for calculating and clustering the intersection of the region with the faces of a cube circumscribing the sub volume; apparatus for calculating approximated centerline paths from the current endoscope position to the center of each cluster formed in the preceding step; apparatus for comparing each of the centerline paths with a current path exhibited by the endoscope; apparatus for assigning a score based on the comparing, to each of the centerline paths; and apparatus for selecting a centerline path based on the score.

In accordance with another aspect of the invention, apparatus for centering and smoothing the initial path comprises apparatus for: setting a sphere at a vertex location; increasing the size of the sphere size until it comes into collision with a wall of the lumen; calculating a translation force from the collision; applying the translation force until the sphere is no longer in collision; increasing the size of the sphere and it again comes into further collision with the wall; calculating a further translation force; applying the further translation force until the sphere is no longer in collision; repeating the foregoing three steps until the sphere reaches a final position where it cannot grow any more without collision; indicating the final position as a final vertex position.

In accordance with another aspect of the invention, a method for automatic local path planning for a virtual endoscope comprises the steps of defining a sub volume around a current endoscope position in a lumen; performing a region growing inside the lumen, starting from the current endoscope position; calculating and clustering the intersection of the region with the faces of a cube circumscribing the sub volume; calculating approximated centerline paths from the current endoscope position to the center of each cluster formed in the preceding step; comparing each of the centerline paths with a current path exhibited by the endoscope; and selecting an optimal centerline path based on the comparison.

BRIEF DESCRIPTION OF THE SEVERAL VIEWS OF THE DRAWINGS

These and other aspects of the present invention will be more fully understood from the detailed description which follows, in conjunction with the drawing, in which.

DETAILED DESCRIPTION OF THE INVENTION

It will be understood that the method and system of the present invention are implemented utilizing a programmable digital computer and that the operations herein described are in reference to such an implementation. In the context of imaging, terms such as "air", "lumen", etc. are typically intended to refer to the corresponding imaging of these features.

Figure 1:
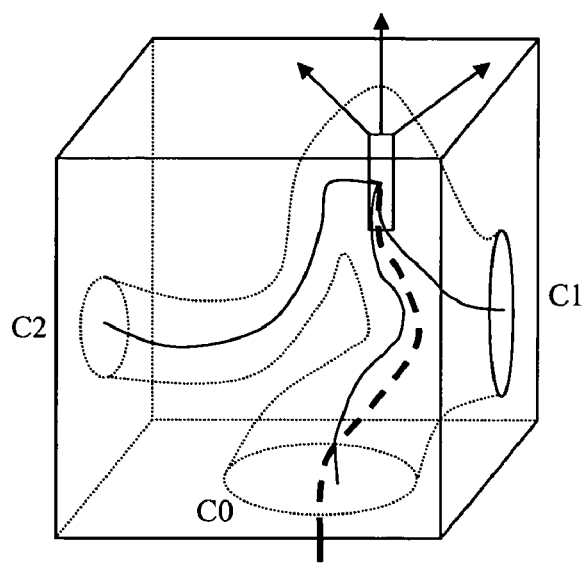
FIG. 1 shows diagrammatically a typical situation, helpful to a fuller understanding of the present invention, wherein the progress of an endoscope is stuck in a sharp bend.

As hereinbefore explained, it is possible, under certain circumstances, for operation of prior-art systems for virtual colonoscopy to get stuck in a sharp bend, or a deep Haustral fold as may occur in virtual colonoscopy. FIG. 1 shows a typical situation where the endoscope is stuck in a sharp bend.

In accordance with embodiment of the present invention, a region grown from the endoscope position intersects the cube in three clusters, c0, c1 and c2. The system calculates new centerlines from the endoscope towards the center of each cluster and compares each path with the path of the endoscope. A score is calculated, which reflects the dissemblance of the path with the incoming path. The path with the highest score is most likely the one that continues in the direction of the colon. If there is only one cluster, the system decides that there is a block and that it has reached a dead end.

In accordance with an embodiment of the present invention, a method for automatic path planning includes a step of defining a sub volume around the current endoscope position. Next, a step of performing a region growing inside the lumen is carried out, starting from the endoscope position. This is followed by the steps of calculating and clustering the intersection of the grown region with the 6 faces of the cube circumscribing the region of interest. Approximated centerlines from the endoscope position to the center of each of the clusters are then calculated. Each path is compared with the current path of the endoscope and a best score is found.

The step of calculating approximated centerlines may be performed in any of various ways. A number of centerline algorithms use thinning, morphological operators, distance transforms, minimum cost paths, Dijkstra's algorithm, etc. Background material may be found in the literature, for example:

Zhou et al., "Three-Dimensional Skeleton and Centerline Generation Based on an Approximate Minimum Distance Field," The Visual Computer, 14:303–314 (1998); R. Truyen, T. Deschamps, L. D. Cohen, "Clinical evaluation of an automatic path tracker for virtual colonoscopy," Medical Image Computing and Computer-Assisted Intervention (MICCAI), Utrecht, Netherlands, October 2001; Chen et al., "A Fast Algorithm to Generate Centerline for Virtual Colonoscopy," SPIE Conference, Feb. 12–18, 2000; Richard Robb, "Virtual (Computed) Endoscopy: Development and Evaluation Using the Visible Human Datasets," Oct. 7–8, 1996, www.mayo.edu; U.S. Pat. No. 6,514,082 entitled "System and method for performing a three-dimensional examination with collapse correction."

Another way of carrying out colon segmentation comprises performing a start- and endpoint calculation, and performing an initial path calculation as described in the afore-mentioned provisional patent application No. 60/470,579 by Geiger et al. This is followed by path centering and smoothing. This starts typically with a colon dataset that has been obtained using a colonoscopy protocol typically including bowel preparation and air insufflation. The dataset is segmented by applying a threshold to air and doing connected component analysis, whereby connected components that do not belong to the colon are discarded, either automatically or by manual selection. Starting from a first voxel that belongs to the colon, distance labeling of voxels is carried out, typically with consecutive numbering, the first voxel getting label 0, its neighbors label 1, their neighbors label 2, and so forth. A search is performed for the highest label, this becoming the starting point p0. From p0, a new distance label map is created by repeating the prior step of distance labeling and obtaining another voxel with the highest number. This is the endpoint p1.

Figure 2:
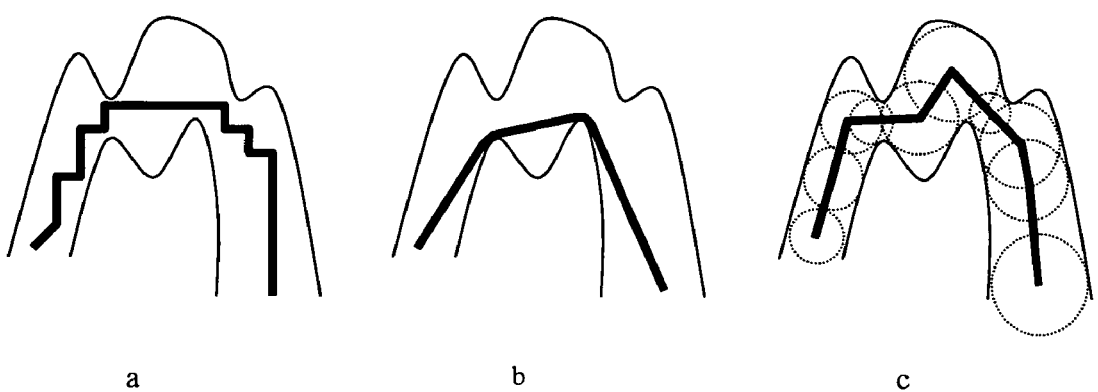
FIGS. 2 and 3 show voxel paths relating to centerline extraction as may be utilized in embodiments of the present invention.
Figure 3:
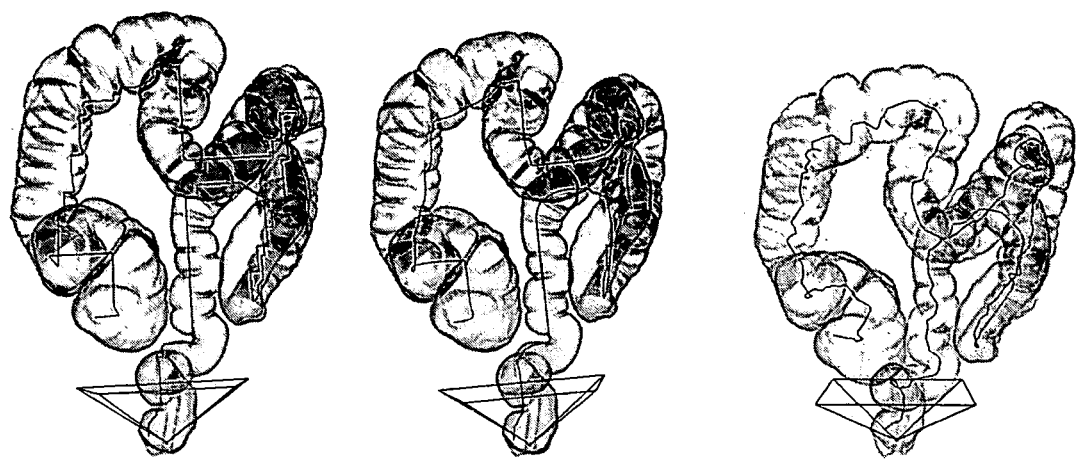

From p1, distance labels are used to get a path of connected voxels that ends in p0. This is done by searching among the neighbors of p2 for a voxel with a smaller label, and so forth, until p0 is reached. See FIG. 2a and FIG. 3a which show the initial voxel path. The resulting path is generally jagged and is smoothed by using known techniques, for example, Gaussian smoothing. Any vertex is replaced by the weighted average of its n neighbors, and the process is repeated over a number of iterations. Any new vertex position will be tested for collision with the colon wall by verifying whether the new coordinate still lies within the segmented colon. In the event of a collision, the vertex is left at the last collision-free position. In a sense, this process may be likened to the path of a stretched flexible weightless string passing through the colon. See FIG. 2b and FIG. 3b which show the initial smoothing step. FIGS. 2(c) and 3(c) show the final centering.

In accordance with a described embodiment, this smooth path is centered using spheres with increasing sizes. See FIG. 4. A small sphere is centered at a vertex along the path. The vertices on this sphere are checked for collision with the colon wall. If the vertices are in a collision, a force is defined based on the sphere normals. This force is used to move the sphere away from the wall. The sphere is constrained to move on a plane perpendicular to the path. If the sphere is no longer in collision, the size of the sphere is increased and the collision calculation and shift is repeated, the process stopping when the sphere cannot be further shifted and/or increased in size without creating a collision. Te center of the sphere is now taken as the new position for the vertex. The process repeats for the next vertex of the trajectory or path. See FIG. 1c. A description of the collision detection technique and calculation of translation force is given in a publication by Geiger, B., "Real-Time Collision Detection and Response for Complex Environments," Computer Graphics International 2000; Jun. 19–23, 2000; Geneva, Switzerland. However, the collision detection and force calculation herein is done directly on the voxel, rather than on polyhedral reconstructions, although it generally follows the ideas outlined in the aforementioned paper by Geiger. Thereafter, and after centering, the path undergoes another Gaussian smoothing with collision control, this time using fewer iterations and a smaller neighborhood.

Figure 4:
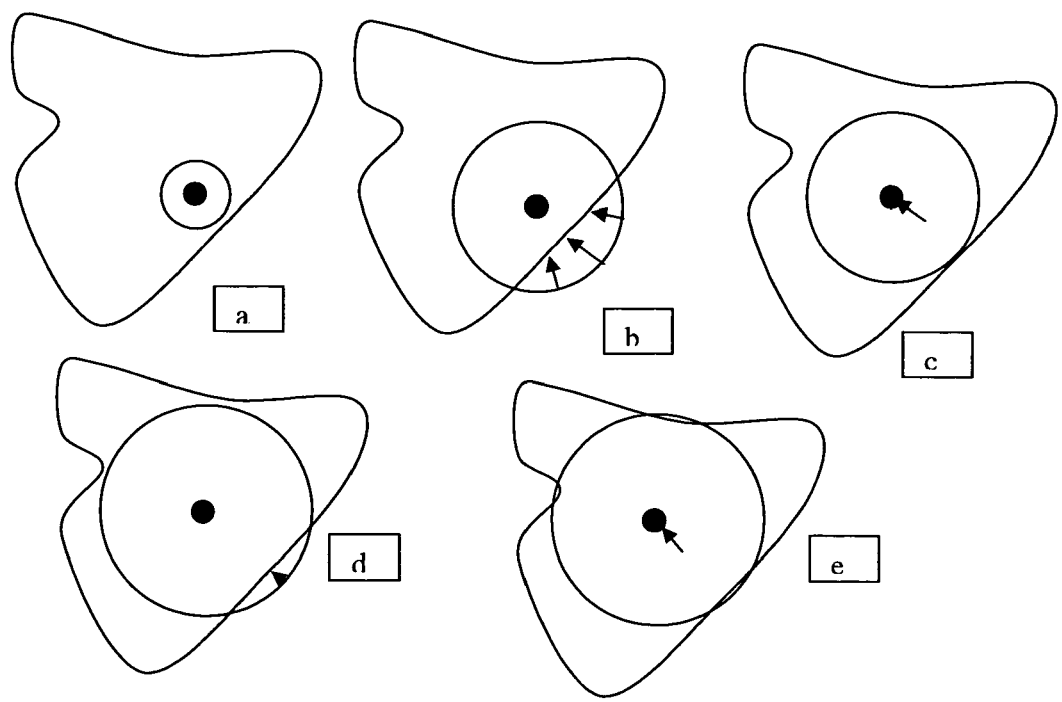
FIG. 4 shows a centering step as may be utilized in embodiments of the present invention.

FIG. 4 shows the summarized procedure for the centering step: a sphere is set at the vertex location (a); the sphere size is increased until it collides with the wall. From the collision, a translation force is calculated (b). The translation is applied until the sphere is no longer in collision (c). The size of the sphere is again increased and it is now colliding with the wall. A translation is calculated (d). After translation, the sphere reaches a position where it cannot grow any more. This represents the final vertex position (c).

A preferred way, in accordance with the principles of the present invention and which does not use such morphological operations, is faster in certain situations.

In accordance with an embodiment of the invention, a method for automatic local path planning for virtual colonoscopy comprises the following steps.

Automatic segmentation is performed wherein the automatic segmentation cuts out a block of a selected cube size, (for example 128×128×128) voxels centered at the position of the endoscope. Starting with the voxel containing the endoscope as a seed, a region growing inside air is performed. All voxels containing air and belonging to the same lumen are labeled. This air column intersects the cube at various locations. These locations are clustered, whereby voxels that share faces are added to the same cluster, and the center of each cluster is calculated by averaging the voxel coordinates of voxels of each cluster. Centerlines are calculated from the center of each cluster to the endoscope position. Each centerline is compared to the path of the endoscope. Starting from the endoscope position, the absolute value of the difference of points on a centerline is added to the corresponding point on the endoscope path. The sum is divided by the length to provide a score. The higher this score, the more distant is the centerline from the incoming path. The path with the highest score is the best candidate to follow. If there is only one path, it is most likely the one that the endoscope moved in, and the system knows there is a dead end.

It will be understood that the invention, which has been described primarily in the context of virtual colonoscopy in which it is most useful, is nevertheless also applicable to various other virtual endoscopic type examinations. While the invention has been described by way of exemplary embodiments, it will also be understood by one of skill in the art to which it pertains that various changes and modifications can be made which do not depart from the spirit of the invention which is defined by the claims following.

What is claimed is:

1. A method for automatic local path planning for a virtual endoscope, comprising the steps of:
    deriving a colon dataset obtained by a colonoscopy protocol for utilization in subsequent steps;
    defining a sub volume around a current endoscope position in a lumen;
    performing a region growing inside said lumen, starting from said current endoscope position;
    calculating and clustering the intersection of said region with the faces of a cube circumscribing said sub volume;
    calculating approximated centerline paths from said current endoscope position to the center of each cluster formed in the preceding step;
    comparing each of said centerline paths with a current path exhibited by said endoscope;
    assigning a score based on said comparing, to each of said centerline paths; and
    selecting a centerline path based on said score.

2. A method in accordance with claim 1, wherein said step of deriving a colon dataset obtained by a colonoscopy protocol comprises deriving said data set by computerized tomography (CT).

3. A method in accordance with claim 1, wherein said step of deriving a colon dataset obtained by a colonoscopy protocol comprises deriving said data set by magnetic resonance (MR).

4. A method in accordance with claim 1, including a step of defining said cube to be of a given number of voxels centered around said current endoscope.

5. A method in accordance with claim 1, including the steps of:
    region growing inside "air" within said lumen; and
    labeling all voxels in said air within said lumen.

6. A method in accordance with claim 1, including steps of:
    forming a cluster at each location wherein said air within said lumen intersects a corresponding face of said cube;
    including in each said cluster voxels that share a face corresponding to said cluster.

7. A method in accordance with claim 6, including step of:
    calculating the center of each cluster by averaging voxel coordinates of voxels of each of said clusters.

8. A method in accordance with claim 7, including step of:
    calculating respective centerline paths from said center of each cluster to said current endoscope position.

9. A method in accordance with claim 1, wherein said step of assigning a score based on said comparing, to each of said centerline paths comprises:
    starting from said current endoscope position, forming the sum of the absolute values of the difference of points on a respective centerline path to a corresponding point on said current path exhibited by said endoscope;
    dividing said sum by length of said respective centerline path to form a quotient score; and
    selecting a path having the highest quotient score.

10. A method in accordance with claim 9, including step of detecting when only one centerline path exists and indicating such a result as a dead end.

11. A method in accordance with claim 1, wherein said step of calculating approximated centerline paths comprises:
    calculating an initial path; and
    centering and smoothing said initial path.

12. A method in accordance with claim 11 wherein said step of calculating an initial path comprises:
    from said endpoint, successively storing voxels with decreasing label numbers until reaching said start point.

13. A method in accordance with claim 11 wherein said step of centering and smoothing said initial path comprises using Gaussian smoothing.

14. A method in accordance with claim 13, wherein said step of centering and smoothing said initial path comprises:
    setting a sphere at a vertex location;
    increasing the size of said sphere size until it comes into collision with a wall of said lumen;
    calculating a translation force from said collision;
    applying said translation force until said sphere is no longer in collision;
    increasing the size of said sphere and it again comes into further collision with said wall;
    calculating a further translation force;
    applying said further translation force until said sphere is no longer in collision;
    repeating the foregoing three steps until said sphere reaches a final position where it cannot grow any more without collision;
    indicating said final position as a final vertex position.

15. A method for automatic local path planning for a virtual endoscope, comprising the steps of:
    deriving a colon dataset obtained by a colonoscopy protocol for utilization in subsequent steps;
    defining a sub volume around a current endoscope position in a lumen;
    performing a region growing inside said lumen, starting from said current endoscope position;
    calculating and clustering the intersection of said region with the faces of a cube circumscribing said sub volume;

calculating approximated centerline paths from said current endoscope position to the center of each cluster formed in the preceding step by:
  calculating an initial path;
  centering and smoothing said initial path;
comparing each of said centerline paths with a current path exhibited by said endoscope;
assigning a score based on said comparing, to each of said centerline paths; and
selecting a centerline path based on said score.

16. A method in accordance with claim 15, wherein said step of deriving a colon dataset obtained by a colonoscopy protocol comprises deriving said data set by computerized tomography (CT).

17. A method in accordance with claim 15, wherein said step of deriving a colon dataset obtained by a colonoscopy protocol comprises deriving said data set by magnetic resonance (MR).

18. A method for automatic local path planning for a virtual endoscope, comprising the steps of:
  defining a sub volume around a current endoscope position in a lumen;
  performing a region growing inside said lumen, starting from said current endoscope position;
  calculating and clustering the intersection of said region with the faces of a cube circumscribing said sub volume;
  calculating approximated centerline paths from said current endoscope position to the center of each cluster formed in the preceding step;
  comparing each of said centerline paths with a current path exhibited by said endoscope; and
  selecting an optimal centerline path based on said comparing.

19. A system for automatic local path planning for a virtual endoscope, comprising:
  means for defining a sub volume around a current endoscope position in a lumen;
  means for performing a region growing inside said lumen, starting from said current endoscope position;
  means for calculating and clustering the intersection of said region with the faces of a cube circumscribing said sub volume;
  means for calculating approximated centerline paths from said current endoscope position to the center of each cluster formed in the preceding step;
  means for comparing each of said centerline paths with a current path exhibited by said endoscope; and
  means for selecting an optimal centerline path based on said comparing.

20. A system for automatic local path planning for a virtual endoscope, comprising:
  means for deriving a colon dataset obtained by a colonoscopy protocol for utilization in subsequent steps;
  means for defining a sub volume around a current endoscope position in a lumen;
  means for performing a region growing inside said lumen, starting from said current endoscope position;
  means for calculating and clustering the intersection of said region with the faces of a cube circumscribing said sub volume;
  means for calculating approximated centerline paths from said current endoscope position to the center of each cluster formed in the preceding step;
  means for comparing each of said centerline paths with a current path exhibited by said endoscope;
  means for assigning a score based on said comparing, to each of said centerline paths; and
  means for selecting a centerline path based on said score.

21. A system in accordance with claim 20, wherein said means for deriving a colon dataset obtained by a colonoscopy protocol comprises means for deriving said data set by computerized tomography (CT).

22. A system in accordance with claim 20, wherein said means for deriving a colon dataset obtained by a colonoscopy protocol comprises means for deriving said data set by magnetic resonance (MR).

23. A system in accordance with claim 20, including means for defining said cube to be of a given number of voxels centered around said current endoscope.

24. A system in accordance with claim 20, including means for:
  region growing inside "air" within said lumen; and
  labeling all voxels in said air within said lumen.

25. A system in accordance with claim 20, including means for:
  forming a cluster at each location wherein said air within said lumen intersects a corresponding face of said cube;
  including in each said cluster voxels that share a face corresponding to said cluster.

26. A system in accordance with claim 25, including means for:
  calculating the center of each cluster by averaging voxel coordinates of voxels of each of said clusters.

27. A system in accordance with claim 26, including means for:
  calculating respective centerline paths from said center of each cluster to said current endoscope position.

28. A system in accordance with claim 20, wherein said means for assigning a score based on said comparing, to each of said centerline paths comprises means for:
  starting from said current endoscope position, forming the sum of the absolute values of the difference of points on a respective centerline path to a corresponding point on said current path exhibited by said endoscope;
  dividing said sum by length of said respective centerline path to form a quotient score; and
  selecting a path having the highest quotient score.

29. A system in accordance with claim 28, including means for detecting when only one centerline path exists and indicating such a result as a dead end.

30. A system in accordance with claim 20, wherein said means for calculating approximated centerline paths comprises means for:
  calculating an initial path; and
  centering and smoothing said initial path.

31. A system in accordance with claim 30 wherein said means for calculating an initial path comprises means for:
  from said endpoint, successively storing voxels with decreasing label numbers until reaching said start point.

32. A system in accordance with claim 30 wherein said means for centering and smoothing said initial path comprises means for using Gaussian smoothing.

33. A system in accordance with claim 30, wherein said means for centering and smoothing said initial path comprises means for:
  setting a sphere at a vertex location;
  increasing the size of said sphere size until it comes into collision with a wall of said lumen;
  calculating a translation force from said collision;
  applying said translation force until said sphere is no longer in collision;

increasing the size of said sphere and it again comes into further collision with said wall;

calculating a further translation force;

applying said further translation force until said sphere is no longer in collision;

repeating the foregoing three steps until said sphere reaches a final position where it cannot grow any more without collision;

indicating said final position as a final vertex position.

34. A system for automatic local path planning for a virtual endoscope, comprising means for:

deriving a colon dataset obtained by a colonoscopy protocol for utilization in subsequent steps;

defining a sub volume around a current endoscope position in a lumen;

performing a region growing inside said lumen, starting from said current endoscope position;

calculating and clustering the intersection of said region with the faces of a cube circumscribing said sub volume;

calculating approximated centerline paths from said current endoscope position to the center of each cluster formed in the preceding step by:

calculating an initial path;

centering and smoothing said initial path;

comparing each of said centerline paths with a current path exhibited by said endoscope;

assigning a score based on said comparing, to each of said centerline paths; and selecting a centerline path based on said score.

* * * * *